(12) United States Patent
Chilakabathini et al.

(10) Patent No.: US 12,313,621 B2
(45) Date of Patent: May 27, 2025

(54) METHOD AND SYSTEM FOR ASSESSING HEALTH OF A WOOD SPECIMEN

(71) Applicant: Wipro Limited, Bangalore (IN)

(72) Inventors: Shiny Manasseh Chilakabathini, Khammam (IN); Sujatha Jagannath, Bangalore (IN); Ramachandram Vedula, Bangalore (IN)

(73) Assignee: Wipro Limited, Bangalore (IN)

( * ) Notice: Subject to any disclaimer, the term of this patent is extended or adjusted under 35 U.S.C. 154(b) by 343 days.

(21) Appl. No.: 17/660,853

(22) Filed: Apr. 27, 2022

(65) Prior Publication Data

US 2023/0273182 A1    Aug. 31, 2023

(30) Foreign Application Priority Data

Feb. 28, 2022    (IN) .............................. 202241010553

(51) Int. Cl.
    *G01N 33/46*    (2006.01)
    *G01N 29/04*    (2006.01)
    (Continued)

(52) U.S. Cl.
    CPC ........... *G01N 33/46* (2013.01); *G01N 29/048* (2013.01); *G01N 29/07* (2013.01); *G01N 29/343* (2013.01);
    (Continued)

(58) Field of Classification Search
    CPC ...................................................... G01N 33/46
    See application file for complete search history.

(56) References Cited

U.S. PATENT DOCUMENTS 4,648,276 A * 3/1987 Klepper .............. G01S 7/52025
                                                        73/602
5,533,411 A * 7/1996 Koiwa .................... G01N 29/07
                                                        73/598

(Continued)

FOREIGN PATENT DOCUMENTS

CN            111351860 A       6/2020

OTHER PUBLICATIONS

H. Mu, L. Li, L. Yu, M. Zhang and D. Qi, "Detection and Classification of Wood Defects by ANN," 2006 International Conference on Mechatronics and Automation, 2006, Abstract, doi: 10.1109/ICMA.2006.257659, 1 page.

(Continued)

*Primary Examiner* — Hyun D Park
(74) *Attorney, Agent, or Firm* — Finnegan, Henderson, Farabow, Garrett & Dunner, LLP.

(57) ABSTRACT

Present disclosure discloses method and system for assessing health of a wood specimen. Method receives ultrasonic data for each of a plurality of alignments of a transmitter and associated receiver across a cross-section of one or more cross-sections along a length of the wood specimen. The ultrasonic data comprises a pulse velocity, a transit time and a distance travelled by an ultrasonic pulse between the transmitter and the associated receiver. Thereafter, method measures relative features of the wood specimen using the ultrasonic data. Subsequently, method identifies a condition of the cross-section of the wood specimen based on the relative features using a trained ML model. Upon identifying the condition of the cross-section to be defective, method determines a position of a defect in the cross-section of the wood specimen using the relative features and determines a severity of the defect using the trained ML model and the relative features.

9 Claims, 6 Drawing Sheets

(51) Int. Cl.
*G01N 29/07* (2006.01)
*G01N 29/34* (2006.01)
*G01N 29/36* (2006.01)
*G01N 29/44* (2006.01)

(52) U.S. Cl.
CPC ......... *G01N 29/36* (2013.01); *G01N 29/4445* (2013.01); *G01N 2291/0238* (2013.01)

(56) References Cited

U.S. PATENT DOCUMENTS

| | | | | |
|---|---|---|---|---|
| 6,029,522 | A | * | 2/2000 | Schafer .............. G01N 29/2493 |
| | | | | 73/598 |
| 2014/0216158 | A1 | * | 8/2014 | Sanabria Martin .... G01N 33/46 |
| | | | | 73/588 |

OTHER PUBLICATIONS

Marchetti, Barbara & Munaretto, R. & Revel, G. & Tomasini, Enrico. "Non-Contact Ultrasonic Sensor for Density Measurement and Defect Detection Wood", (2004), ResearchGate, 8 pages.

* cited by examiner

| D | B | G |
|---|---|---|
| F | O | E |
| H | A | C |

METHOD AND SYSTEM FOR ASSESSING HEALTH OF A WOOD SPECIMEN

TECHNICAL FIELD

The present subject matter generally relates to an internal defect detection technique in a wood specimen, more particularly, to a method and a wood health assessment system for assessing health of a wood specimen.

BACKGROUND

Energy distribution and telecommunication segments are the largest consumer of utility poles or wooden logs all over the world. These are predominantly made of wood. All utility companies need to monitor the condition of wooden poles regularly and predict their future condition accurately to operate their energy distribution system continuously and safely. An effective pole inspection program strikes a balance between accurately identifying utility poles that put both system reliability and human life at risk while minimizing the number of still serviceable utility poles being replaced. The existing methods used in identification of defective utility pole or wooden logs are subjective in nature and a lot depends on the intuition and experience of the investigator/pole/log tester. However, due to the complex combination of several factors such as wood species, preservation methods and material, soil and climate conditions, insect and mechanical damage, inspection methodology as well as human errors involved, no fool-proof wood inspection method exists today. Consequently, the existing methods fail to guarantee the condition of a standing utility pole or a wooden log with high accuracy. As a result, many utility poles or wooden logs are replaced unnecessarily, and a significant number of utility poles or wooden logs continue to fail unexpectedly in-service, causing damages to assets as well as human lives. In this context, an automated wooden pole or log inspection and maintenance, specifically with a non-destructive technique, is of interest to companies dealing with utility poles or wooden logs, as well as researchers/ academic institutions.

The information disclosed in this background of the disclosure section is for enhancement of understanding of the general background of the invention and should not be taken as an acknowledgement or any form of suggestion that this information forms the prior art already known to a person skilled in the art.

SUMMARY

Embodiments of the present disclosure may address the above-discussed problem associated with inspection and maintenance of wooden utility poles or wood specimens.

In an embodiment, there is a method provided for assessing health of a wood specimen. The method receives ultrasonic data for each of a plurality of alignments of a transmitter and associated receiver across a cross-section of one or more cross-sections along a length of the wood specimen. The ultrasonic data comprises a pulse velocity, a transit time and a distance travelled by an ultrasonic pulse between the transmitter and the associated receiver. Thereafter, the method measures relative features of the wood specimen using the ultrasonic data received for each alignment of the transmitter and the associated receiver. Subsequently, the method identifies a condition of the cross-section of the wood specimen based on the relative features of the wood specimen using a trained machine learning model. Upon identifying the condition of the cross-section of the wood specimen to be a defective condition, the method determines a position of a defect in the cross-section of the wood specimen using the relative features of the wood specimen and determines a severity of the defect using the trained machine learning model and the relative features of the wood specimen.

In an embodiment, there is a wood health assessment system provided for assessing health of a wood specimen. The wood health assessment system includes a processor and a memory communicatively coupled to the processor, wherein the memory stores processor-executable instructions, which on execution by the processor, cause the processor to receive ultrasonic data for each of a plurality of alignments of a transmitter and associated receiver across a cross-section of one or more cross-sections along a length of the wood specimen. The ultrasonic data comprises a pulse velocity, a transit time and a distance travelled by an ultrasonic pulse between the transmitter and the associated receiver. Thereafter, the processor is configured to measure relative features of the wood specimen using the ultrasonic data received for each alignment of the transmitter and the associated receiver. Subsequently, the processor is configured identify a condition of the cross-section of the wood specimen based on the relative features of the wood specimen using a trained machine learning model. Upon identifying the condition of the cross-section of the wood specimen to be a defective condition, the processor is configured to determine a position of a defect in the cross-section of the wood specimen using the relative features of the wood specimen and determine a severity of the defect using the trained machine learning model and the relative features of the wood specimen.

In an embodiment, there is a non-transitory computer readable medium including instructions stored thereon that when processed by at least one processor cause a wood health assessment system to perform acts of receiving ultrasonic data for each of a plurality of alignments of a transmitter and associated receiver across a cross-section of one or more cross-sections along a length of the wood specimen. The ultrasonic data comprises a pulse velocity, a transit time and a distance travelled by an ultrasonic pulse between the transmitter and the associated receiver. Thereafter, the instructions cause the at least one processor to measure relative features of the wood specimen using the ultrasonic data received for each alignment of the transmitter and the associated receiver. Subsequently, the instructions cause the at least one processor to identify a condition of the cross-section of the wood specimen based on the relative features of the wood specimen using a trained machine learning model. Upon identifying the condition of the cross-section of the wood specimen to be a defective condition, the instructions cause the at least one processor to determine a position of a defect in the cross-section of the wood specimen using the relative features of the wood specimen and determine a severity of the defect using the trained machine learning model and the relative features of the wood specimen.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The accompanying drawings, which are incorporated in and constitute a part of this disclosure, illustrate exemplary embodiments and together with the description, serve to explain the disclosed principles. The same numbers are used throughout the figures to reference like features and components. Some embodiments of system and/or methods in accordance with embodiments of the present subject matter are now described below, by way of example only, and with reference to the accompanying figures.

Figure 1:
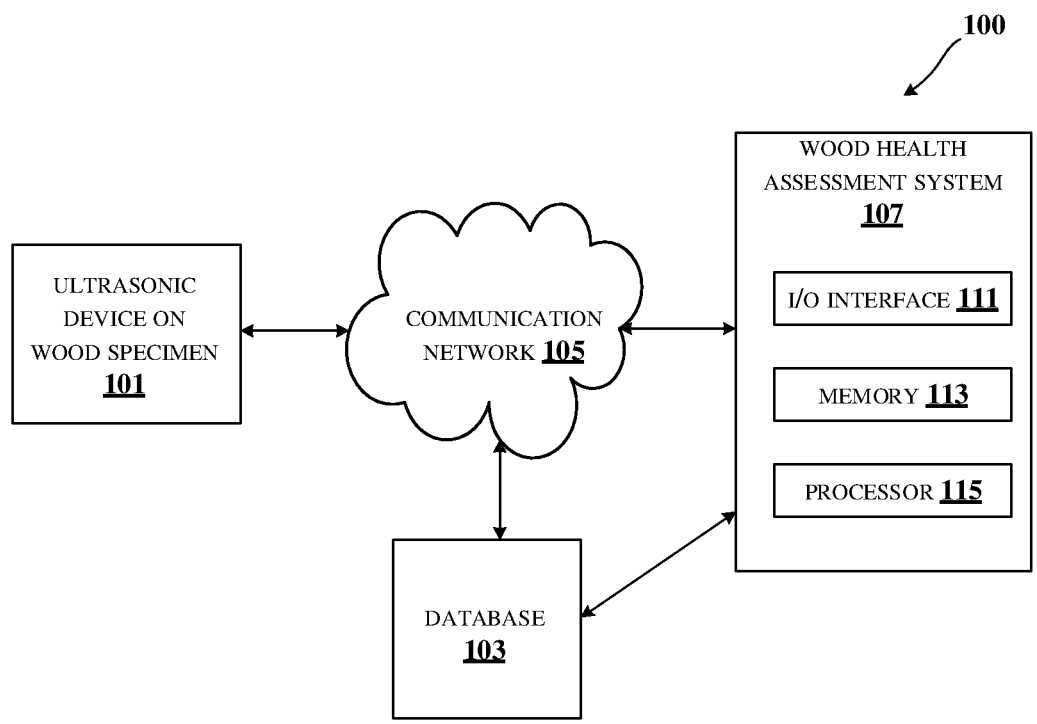
FIG. 1 illustrates an exemplary environment for assessing health of a wood specimen in accordance with some embodiments of the present disclosure.

It should be appreciated by those skilled in the art that any block diagrams herein represent conceptual views of illustrative systems embodying the principles of the present subject matter. Similarly, it will be appreciated that any flowcharts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternatives falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

In the following detailed description of embodiments of the disclosure, reference is made to the accompanying drawings which illustrates specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Embodiments of the present disclosure provides an improved method and a system for health assessment of a wood specimen by detecting defects and providing recommendations using machine learning techniques. The present disclosure uses ultrasonic data captured across a cross-section of a wood specimen using a non-destructive testing method and applies machine learning techniques to the ultrasonic data to accurately identify, position and grade defect in the cross-section of the wood specimen. This process is repeated across more cross-sections along a length of the wood specimen to generate a health record for the wood specimen. The approach presented in the present disclosure has following technical advantages: (1) The present disclosure uses an ultrasonic device for health assessment of a wood specimen, which is a non-destructive testing method. (2) The present disclosure performs analysis and presents results based on relative measurements/relative features such mean, standard deviation, lower limit, upper limit, normalized lower limit, normalized upper limit and the like and not on absolute values, making the results independent of wood species and avoiding re-training of machine learning model for any new wood species. (3) Consequently, this method leads to more standardised testing and evaluation of any wood specimen. (4) The method is easy to use for any utility pole inspector/personnel.

FIG. 1 illustrates an exemplary environment for assessing health of a wood specimen in accordance with some embodiments of the present disclosure.

In the FIG. 1, the environment 100 includes a wood specimen 101 on which an ultrasonic device is positioned/aligned, a database (also, referred as repository) 103, a communication network 105 and a wood health assessment system 107. The wood specimen 101 may be a wooden pole (also, referred as utility pole) or a wooden log or a wooden piece belonging to any wood species. The ultrasonic device comprising of a transmitter and associated receiver may be positioned/aligned on the wood specimen 101 such that ultrasonic pulses emanating from the ultrasonic device propagate through a cross-section of the wooden specimen 101 on which an inspection is carried out. The ultrasonic device captures ultrasonic data for each of a plurality of alignments of the transmitter and the associated receiver across the cross-section of the wood specimen 101. Similarly, the ultrasonic data is captured for each of the plurality of alignments of the transmitter and the associated receiver across multiple cross-sections along a length of the wood specimen 101. The ultrasonic data comprises a pulse velocity, a transit time and a distance travelled by an ultrasonic pulse between the transmitter and the associated receiver. Thereafter, the ultrasonic device sends/transmits the ultrasonic data to the wood health assessment system 107 using the communication network 105 using any of the following, but is not limited to, communication protocols/methods: a direct interconnection, an e-commerce network, a Peer-to-Peer (P2P) network, Local Area Network (LAN), Wide Area Network (WAN), wireless network (for example, using Wireless Application Protocol), Internet, Wi-Fi, Bluetooth and the like. In one embodiment, the ultrasonic device is a part of the wood health assessment system 107, especially, an ultrasonic data capture and recording module (discussed later in detail).

In the embodiment, the wood health assessment system 107 may include an Input/Output (I/O) interface 111, a memory 113, and a processor 115. The I/O interface 111 is configured to receive the ultrasonic data from the ultrasonic device for each of the plurality of alignments of the transmitter and the associated receiver across the cross-section of one or more cross-sections along the length of the wood specimen 101. The I/O interface 111 may employ communication protocols/methods such as, without limitation, audio, analog, digital, monoaural, Radio Corporation of America (RCA) connector, stereo, IEEE®-1394 high speed serial bus, serial bus, Universal Serial Bus (USB), infrared, Personal System/2 (PS/2) port, Bayonet Neill-Concelman (BNC) connector, coaxial, component, composite, Digital Visual Interface (DVI), High-Definition Multimedia Interface (HDMI®), Radio Frequency (RF) antennas, S-Video, Video Graphics Array (VGA), IEEE® 802.11b/g/n/x, Bluetooth, cellular e.g., Code-Division Multiple Access (CDMA), High-Speed Packet Access (HSPA+), Global System for Mobile communications (GSM®), Long-Term Evolution (LTE®), Worldwide interoperability for Microwave access (WiMax®), or the like.

The ultrasonic data received by the I/O interface 111 is stored in the memory 113. The memory 113 is communicatively coupled to the processor 115 of the wood health assessment system 107. The memory 113, also, stores processor-executable instructions which may cause the processor 115 to execute the instructions for assessing health of the wood specimen 101. The memory 113 includes, without limitation, memory drives, removable disc drives, etc. The memory drives may further include a drum, magnetic disc drive, magneto-optical drive, optical drive, Redundant Array of Independent Discs (RAID), solid-state memory devices, solid-state drives, etc.

The processor 115 includes at least one data processor for assessing health of the wood specimen 101. The processor 115 may include specialized processing units such as integrated system (bus) controllers, memory management control units, floating point units, graphics processing units, digital signal processing units, etc.

The database 103 includes health records for historic wood specimens. A health record for a historic wood specimen comprises at least one of condition of one or more cross-sections of the historic wood specimen, a position of defect in the one or more cross-sections of the historic wood specimen, a severity of the defect in the one or more cross-sections of the historic wood specimen, and a visual representation of the position of the defect in the one or more cross-sections of the historic wood specimen. The database 103 is updated at pre-defined intervals of time. These updates relate to health record of current wood specimen under testing for adaptive learning.

Hereinafter, the operation of the wood health assessment system 107 is explained briefly.

The ultrasonic device comprising of the transmitter and the associated receiver is positioned/aligned on the wood specimen 101 such that the ultrasonic pulses emanating from the ultrasonic device propagate through a cross-section of the wooden specimen 101 on which an inspection is carried out. The ultrasonic device captures ultrasonic data for each of a plurality of alignments of the transmitter and the associated receiver across the cross-section of the wood specimen 101. Similarly, the ultrasonic data is captured for each of the plurality of alignments of the transmitter and the associated receiver across multiple cross-sections along a length of the wood specimen 101. The ultrasonic data comprises a pulse velocity, a transit time and a distance travelled by an ultrasonic pulse between the transmitter and the associated receiver. Thereafter, the ultrasonic device sends/transmits the ultrasonic data to the wood health assessment system 107 using the communication network 105. The wood health assessment system 107 receives the ultrasonic data and measures relative features of the wood specimen 101 using the ultrasonic data. The wood health assessment system 107 uses a trained Machine Learning (ML) model to identify a condition of the cross-section of the wood specimen 101 based on the relative features of the wood specimen 101. The ML model/technique is one of, but not limited to, a Support Vector Machine (SVM) model, a Random Forest model, and a Logical Regression model. The condition of the cross-section of the wood specimen 101 is one of a defective condition (containing an internal defect in the wood specimen 101) or a non-defective condition (containing no internal defect in the wood specimen 101). In detail, the wood health assessment system 107 determines whether an internal defect is present or not at the given cross-section of the wood specimen 101 based on the relative features of the wood specimen 101. If no internal defect is detected/present, the wood health assessment system 107 generates a health record for the wood specimen 101. On the other hand, if an internal defect is found to be present/identified at the given cross-section of the wood specimen 101, the wood health assessment system 107 determines a position of the internal defect in the cross-section of the wood specimen 101 using the relative features of the wood specimen 101. Subsequently, the wood health assessment system 107 determines a severity of the internal defect using the trained ML model and the relative features of the wood specimen 101. The wood health assessment system 107 determines the severity of the internal defect by quantifying the internal defect into one of insignificantly defective, mildly defective, defective, and severely defective. Thereafter, the wood health assessment system 107 generates the health record for the wood specimen 101 comprising at least one of the condition of the one or more cross-sections of the wood specimen 101, the position of the defect in the one or more cross-sections of the wood specimen 101, the severity of the defect in the one or more cross-sections of the wood specimen 101, and a visual representation of the position of the defect in the one or more cross-sections of the wood specimen 101.

Figure 2A:
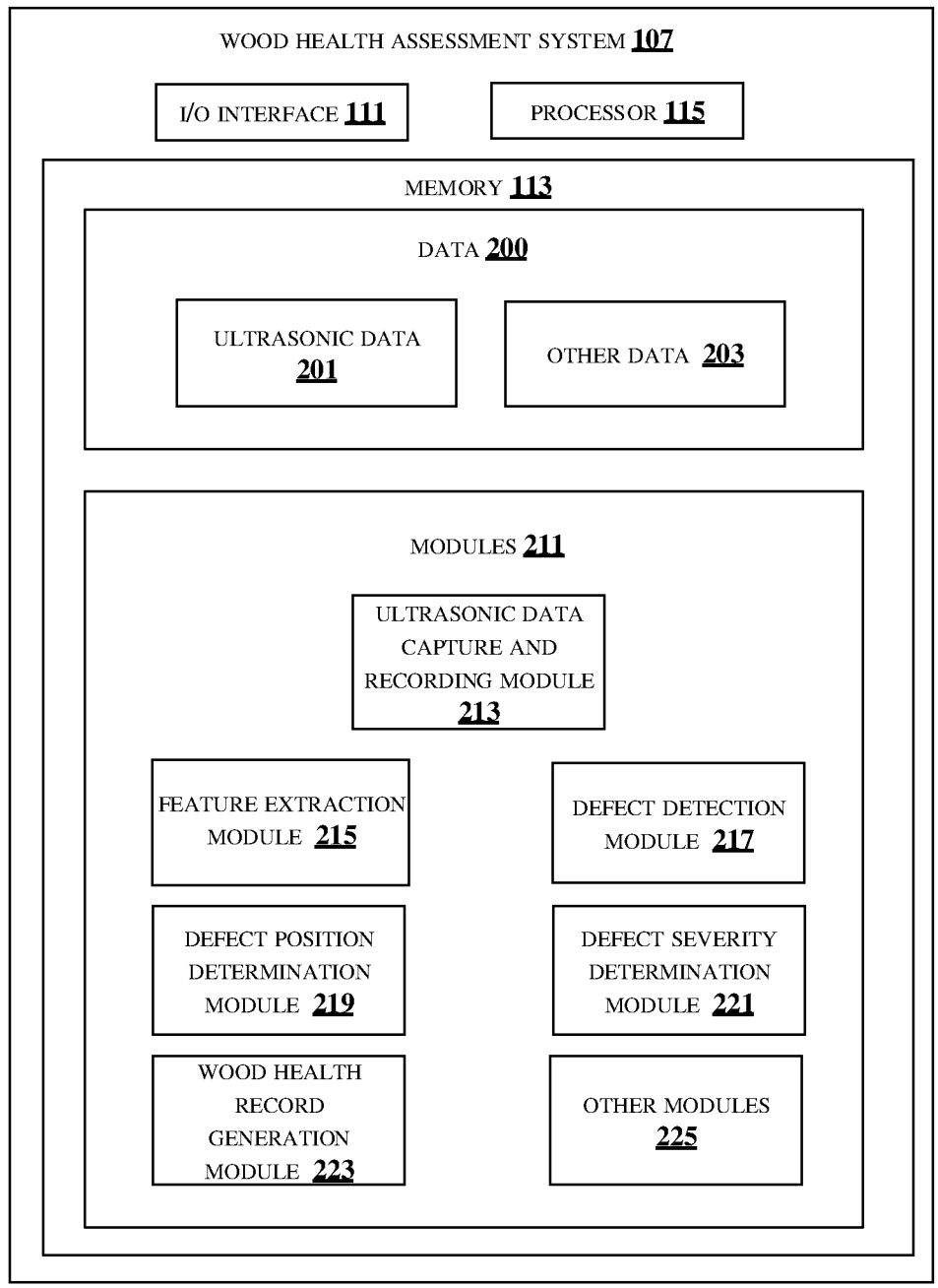
FIG. 2a shows a detailed block diagram of a wood health assessment system in accordance with some embodiments of the present disclosure.

FIG. 2a shows a detailed block diagram of a wood health assessment system in accordance with some embodiments of the present disclosure.

The wood health assessment system 107, in addition to the I/O interface 111 and processor 115 described above, includes data 200 and one or more modules 211, which are described herein in detail. In the embodiment, the data 200 may be stored within the memory 113. The data 200 include, for example, ultrasonic data 201 and other data 203.

The ultrasonic data 201 includes a pulse velocity, a transit time and a distance travelled by an ultrasonic pulse between a transmitter and associated receiver for each of a plurality of alignments of the transmitter and the associated receiver across a cross-section of one or more cross-sections along a length of the wood specimen 101.

The other data 203 stores data, including temporary data and temporary files, generated by one or more modules 211 for performing the various functions of the wood health assessment system 107.

In the embodiment, the data 200 in the memory 113 are processed by the one or more modules 211 present within the memory 113 of the wood health assessment system 107. In the embodiment, the one or more modules 211 are implemented as dedicated hardware units. As used herein, the term module refers to an Application Specific Integrated Circuit (ASIC), an electronic circuit, a Field-Programmable Gate Arrays (FPGA), Programmable System-on-Chip (PSoC), a combinational logic circuit, and/or other suitable components that provide the described functionality. In some implementations, the one or more modules 211 are communicatively coupled to the processor 115 for performing one or more functions of the wood health assessment system 107. The said modules 211 when configured with the functionality defined in the present disclosure results in a novel hardware.

In one implementation, the one or more modules 211 include, but are not limited to, an ultrasonic data capture and recording module 213, a feature extraction module 215, a defect detection module 217, a defect position determination module 219, a defect severity determination module 221, and a wood health record generation module 223. The one or more modules 211, also, includes other modules 225 to perform various miscellaneous functionalities of the wood health assessment system 107.

The ultrasonic data capture and recording module 213: A particular cross-section of the wood specimen 101 is identified. An ultrasonic device comprising of a transmitter and associated receiver is positioned/aligned on the wood specimen 101 such that ultrasonic pulses emanating from the ultrasonic device propagate through the cross-section of the wooden specimen 101 on which an inspection is carried out. The ultrasonic pulses pass through, at a fast pace in a densely compacted wood specimen but takes a longer path if the ultrasonic pulses encounter a defect or a hollow space or a loose wood matter due to fungus/insects. Multiple sets of readings of ultrasonic data are collected with different alignments of the transmitter and the associated receiver across the cross-section for testing i.e., the ultrasonic device captures ultrasonic data for each of a plurality of alignments of the transmitter and the associated receiver across the cross-section of the wood specimen 101. Similarly, the ultrasonic data is captured for each of the plurality of alignments of the transmitter and the associated receiver across multiple cross-sections along a length of the wood specimen 101. Thereafter, the ultrasonic device sends/transmits the ultrasonic data to the wood health assessment system 107 using the communication network 105. In one embodiment, the ultrasonic device is a part of the ultrasonic data capture and recording module 213 of the wood health assessment system 107. The ultrasonic data is analysed to carry out an internal inspection of the wood specimen 101, which is illustrated in detail below:

A particular cross-section of the wood specimen 101 is identified for testing.

Figures 2B, 2C:
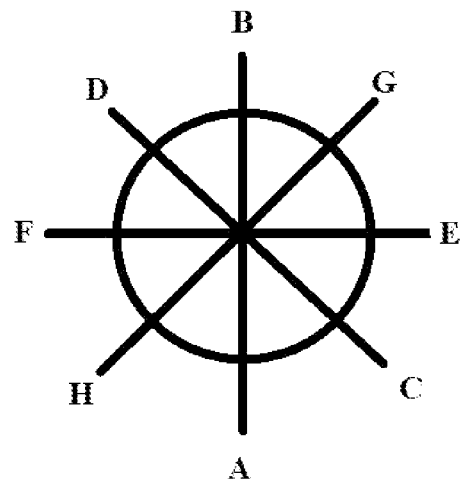
FIG. 2b illustrates an exemplary example of a plurality of alignments of a transmitter and associated receiver across a cross-section of a wood specimen in accordance with some embodiments of the present disclosure.
FIG. 2c illustrates an example of a matrix representation for a position of defect across a cross-section of a wood specimen in accordance with some embodiments of the present disclosure.

A set of transmitter and associated receiver is placed at an alignment, say A-B (as shown in FIG. 2b), to pass ultrasonic pulses across the cross-section of the wood specimen 101. The ultrasonic data comprising a pulse velocity, a transit time and a distance travelled by an ultrasonic pulse between the transmitter and the associated receiver are recorded for the given alignment of measurement. The three parameters are related by the formula $V=D/T$, where D is the distance travelled by the ultrasonic pulse between the transmitter and the associated receiver, T is the transit time and V is the pulse velocity.

The transmitter and the associated receiver are placed at specified alignments as shown in the FIG. 2b.

The ultrasonic device measures 40 combinations of alignments per cross-section, namely, A-E, A-G, A-B, A-D, A-F, B-F, B-H, B-A, B-C, B-E, C-G, C-B, C-D, C-F, C-H, D-H, D-A, D-C, D-E, D-G, E-B, E-D, E-F, E-H, E-A, F-A, F-C, F-E, F-G, F-B, G-D, G-F, G-H, G-A, G-C, H-C, H-E, H-G, H-B, H-D. For any given point, the points immediately adjacent are excluded. For example, for point A, C and H are excluded. As there are 8 points A to H, there will be total of 8×5 i.e., 40 combinations.

With the transmitter and the associated receiver positioned at each of the above-mentioned alignments, the ultrasonic data i.e., V, D and T are recorded.

The feature extraction module 215: Since the pulse velocity, the transit time and the distance travelled by the ultrasonic pulse between the transmitter and the associated receiver alone are insufficient to detect, locate and determine the severity of an internal defect in the wood specimen 101, measuring relative features, which are informative, discriminating and non-dependent, of the wood specimen 101 is important. Hence, the feature extraction module 215 measures/derives relative features of the wood specimen 101 using the ultrasonic data received for each alignment of the transmitter and the associated receiver. The relative features comprise a mean of pulse velocities, a standard deviation of pulse velocities, a lower limit of pulse velocities, an upper limit of pulse velocities, a normalized lower limit of pulse velocities and a normalized upper limit of pulse velocities. The different relative features measured by the feature extraction module 215 are enumerated below:

The alignments corresponding to angle 90 are A-E, C-G, E-B, G-D, B-F, D-H, F-A, H-C. These alignments are represented as Align_90.

Similarly, the alignments representing all angles are listed below:

$$\text{Align\_90}=[A\text{-}E, C\text{-}G, E\text{-}B, G\text{-}D, B\text{-}F, D\text{-}H, F\text{-}A, H\text{-}C]$$

$$\text{Align\_135}=[A\text{-}G, C\text{-}B, E\text{-}D, G\text{-}F, B\text{-}H, D\text{-}A, F\text{-}C, H\text{-}E]$$

$$\text{Align\_180}=[A\text{-}B, C\text{-}D, E\text{-}F, G\text{-}H, B\text{-}A, D\text{-}C, F\text{-}E, H\text{-}G]$$

$$\text{Align\_225}=[A\text{-}D, C\text{-}F, E\text{-}H, G\text{-}A, B\text{-}C, D\text{-}E, F\text{-}G, H\text{-}B]$$

$$\text{Align\_270}=[A\text{-}F, C\text{-}H, E\text{-}A, G\text{-}C, B\text{-}E, D\text{-}G, F\text{-}B, H\text{-}D]$$

The different relative features are calculated as below:

Mean of pulse velocities is calculated which gives 5 mean values corresponding to 5 angles i.e., 90, 135, 180, 225 and 270. These are notated as Mean_90, Mean_135, Mean_180, Mean_225 and Mean_270.

Standard Deviation (SD) of pulse velocities is calculated which gives 5 standard deviation values corresponding to 5 angles i.e., 90, 135, 180, 225 and 270. These are notated as SD_90, SD_135, SD_180, SD_225 and SD_270.

Lower limit of pulse velocities is calculated as Lower limit=Mean−SD for corresponding to 5 angles i.e., 90, 135, 180, 225 and 270, which gives:

$$\text{Lower limit\_90}=\text{Mean\_90}-SD\_90$$

$$\text{Lower limit\_135}=\text{Mean\_135}-SD\_135$$

$$\text{Lower limit\_180}=\text{Mean\_180}-SD\_180$$

Lower limit_225=Mean_225−*SD*_225

Lower limit_270=Mean_270−*SD*_270

Similarly, Upper limit of pulse velocities is calculated as Upper limit=Mean+SD for corresponding to 5 angles i.e., 90, 135, 180, 225 and 270, which gives:

Upper limit_90=Mean_90+*SD*_90

Upper limit_135=Mean_135+*SD*_135

Upper limit_180=Mean_180+*SD*_180

Upper limit_225=Mean_225+*SD*_225

Upper limit_270=Mean_270+*SD*_270

Normalized lower limit (D_L) of pulse velocities is calculated as D_L=pulse velocity at an alignment with respect to an angle−lower limit with respect to the same angle. This gives 40 values corresponding to 40 alignments.

Similarly, normalized upper limit (D_U) of pulse velocities is calculated as D_U=pulse velocity at an alignment with respect to an angle−upper limit with respect to the same angle. This gives 40 values corresponding to 40 alignments.

The defect detection module 217: The relative features of the wood specimen 101 are used by the defect detection module 217 to identify a condition of the cross-section of the wood specimen 101. The defect detection module 217 uses a trained ML model to identify the condition. The ML model/technique is one of, but not limited to, a Support Vector Machine (SVM) model, a Random Forest model, and a Logical Regression model. The condition of the cross-section of the wood specimen 101 is one of the defective condition or a non-defective condition. In this case, the defect detection module 217 feeds the relative features of the wood specimen 101 into a ML model which uses the relative features to learn by itself to predict the results when new data i.e., new relative features is fed for testing. A description of training, testing and analysis by the ML model of the defect detection module 217 is illustrated below.

There are 8 readings obtained per alignment (as shown in the FIG. 2b). These are averaged to get 40 data samples corresponding to 40 alignments and these are represented in a Matrix "K" with 40 rows×3 columns. The columns correspond to the pulse velocity, the transit time and the distance travelled by an ultrasonic pulse between the transmitter and the associated receiver. Further, the two relative features D_L and D_U as measured by the feature extraction module 215, is appended to a data set (for respective alignments) so as to make the matrix "K" as 40 rows and columns. The presence of the defect at the cross-section is determined by the variations of pulse velocities among all 40 alignments. To represent this, the matrix K is converted to a column matrix of size 200*1. The condition of the cross-section of the wood specimen 101 is classified into 2 classes/conditions i.e., Non-Defective (ND) and Defective (D). This "Class/Condition" feature value is appended to the matrix "K" which makes its size to be 201*1.

The data set will contain such "K" matrices of similar size which are measured/computed and gathered from variety of wood species from wood logs of different geographical conditions with variety of defects and defect sizes.

When a new wood specimen is tested, the data set is split into training data which constitutes 80% of the data set and testing data, which constitutes 20% of data set. The training data is further split into X_train and Y_train where X_train has N number of rows and 200 features and Y_train contains N number of rows and one feature namely "Class/Condition" which is the output feature. The defect detection module 217 performs "One Hot Encoding" method to map the output feature so as to represent the categorical data (Classes/Conditions) in binary vectors. The ML model will have 200 input nodes corresponding to 200 input features, X number of hidden layers, and 2 output nodes corresponding to 2 different classes/conditions. The ML model uses the efficient "Adam gradient descent" or a similar optimization algorithm with a logarithmic loss function called "categorical crossentropy". The defect detection module 217 evaluates the ML model by K-fold cross validation method. The defect detection module 217 shuffles the testing data set and creates 10 folds to perform the evaluation. The ML model after getting trained is saved. During testing, the defect detection module 217 loads the saved/trained ML model and feeds the new data sample on which it is predicted as to be either defective condition or non-defective condition. If the ML model of the defect detection module 217 identifies the cross-section of the wood specimen 101 as defective condition, which means there is an internal defect present, the wood health assessment system 107 continues with the defect position determination module 219 and the defect severity determination module 221. If the ML model of the defect detection module 217 identifies the cross-section of the wood specimen 101 as non-defective condition, which means there is no internal defect present, the wood health assessment system 107 moves to the wood health record generation module 223 i.e., the defect position determination module 219 and the defect severity determination module 221 are skipped.

The defect position determination module 219: As the defect detection module 217 in the previous step identified the presence of an internal defect, the purpose of the defect position determination module 219 is to determine a position of the defect in the cross-section of the wood specimen 101 using the relative features of the wood specimen 101. In this case, the entire cross-section of the wood specimen 101 is divided into "T" regions, which is represented by a matrix of size M×N, where T=M×N. The output of the defect position determination module 219 is to visually represent these M×N regions with a color code across the range of values. The color that represents the highest value in the given range indicates presence of defect. A description of analysis and output for a visual representation of 3×3 matrix by the defect position determination module 219 is illustrated below.

Figure 2D:
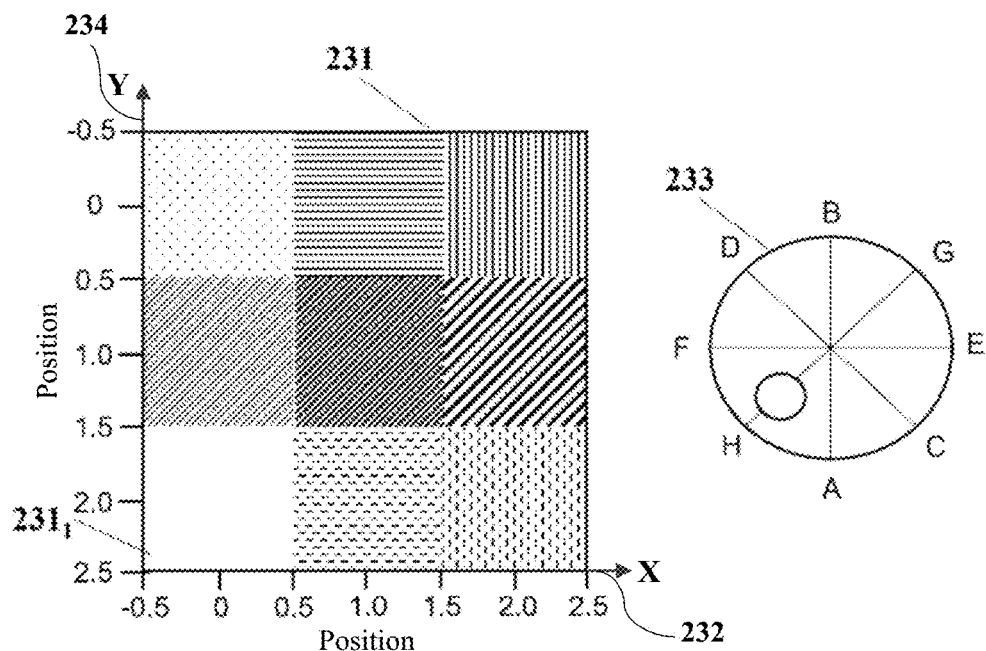
FIGS. 2d-2e illustrate examples of a visual representation of a position of a defect in one or more cross-sections of a wood specimen in accordance with some embodiments of the present disclosure.
Figure 2E:
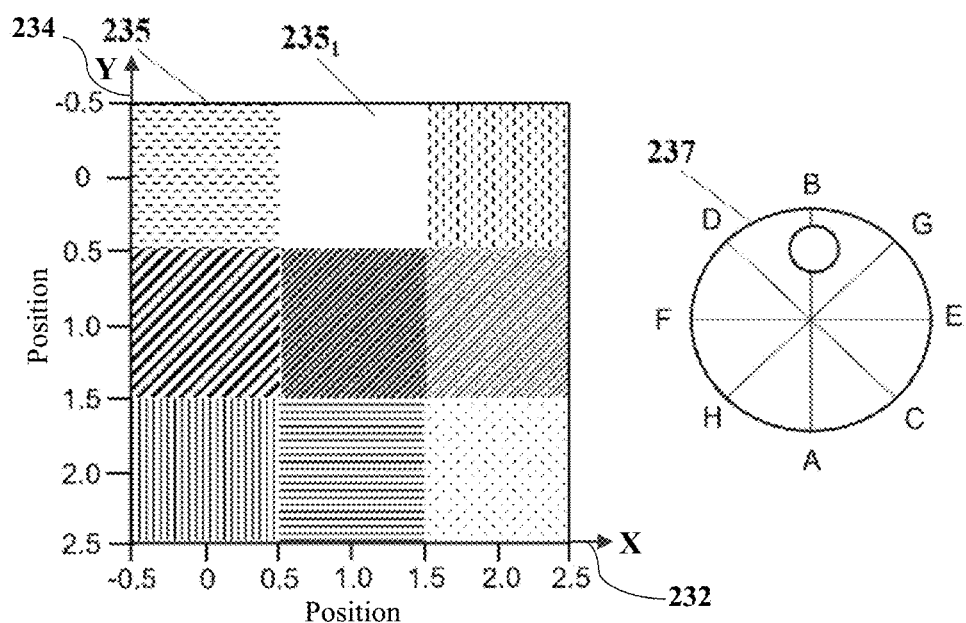

There are 40 averaged transit time values corresponding to 40 alignments per cross section. The defect position determination module 219 calculates/determines mean and standard deviation of these 40 averaged transit time values and the lower limit (=mean−standard deviation). Thereafter, the defect position determination module 219 calculates/determines a difference value for each of the alignment as difference value (=transit time at an alignment−lower limit). From the above set, the defect position determination module 219 considers only those values that correspond to alignment angles 135, 180 and 225. All other values are ignored. The defect position determination module 219 then creates a matrix of 3×3 (as shown in FIG. 2c). For the given 8 segments, from A-H, the defect position determination module 219 attaches weights to each block of the matrix with their difference value in accordance with their alignment. For example, if the difference value is 20 for alignment A-B, then the defect position determination module 219 adds to each of the A and B blocks in the matrix. A partial weight of ⅛ of the difference value is added to the center block O. Further, the defect position determination module 219 normalizes the weights corresponding to each point, such that the values remain between 0 and 1. The defect position determination module 219 then represents this matrix in a patterned format (reference 231 in FIG. 2d and reference 235 in FIG. 2e). The absence of pattern (reference 231 1) in FIG. 2d and (reference 235 1) in FIG. 2e corresponds to position of defect shown in reference 233 in FIG. 2d and reference 237 in FIG. 2e, respectively. In FIG. 2d and FIG. 2e, the position of the defect is represented along an X-axis (denoted by 232) and a Y-axis (denoted by 234) respectively. In FIG. 2d, the defect in a sample wood specimen 233 is located at H with the resulting visual representation of the matrix 231. In FIG. 2e, the defect in a sample wood specimen 237 is located at B with the resulting visual representation of the matrix 235. It is seen that the defect position is pointed to the actual defect position in the sample wood specimen.

The defect severity determination module 221: The relative features of the wood specimen 101 are used by the defect severity determination module 221 to determine a severity of the defect. The defect severity determination module 221 uses a trained ML to determine the severity of the defect. The severity of the defect in the cross-section of the wood specimen 101 is one of insignificantly defective, mildly defective, defective, and severely defective. In this case, the defect severity determination module 221 feeds the relative features of the wood specimen 101 into a ML model which uses the relative features to learn by itself to quantify the defects when new data i.e., new relative features is fed for testing. A description of training, testing and analysis by the ML model of the defect severity determination module 221 is illustrated below.

There are 8 readings obtained per alignment (as shown in the FIG. 2b). These are averaged to get 40 data samples corresponding to 40 alignments and these are represented in a Matrix "K" with 40 rows x 3 columns. The columns correspond to the pulse velocity, the transit time and the distance travelled by an ultrasonic pulse between the transmitter and the associated receiver. Further, the two relative features D_L and D_U as measured by the feature extraction module 215, is appended to a data set (for respective alignments) so as to make the matrix "K" as 40 rows and 5 columns. The presence of the defect at the cross-section is determined by the variations of pulse velocities among all 40 alignments. To represent this, the matrix K is converted to a column matrix of size 200*1. The severity of the defect in the cross-section of the wood specimen 101 is classified into 4 classes i.e., insignificantly defective, mildly defective, defective, and severely defective. This "Severity" feature value is appended to the matrix "K" which makes its size to be 201*1.

The data set will contain such "K" matrices of similar size which are measured/computed and gathered from variety of wood species from wood logs of different geographical conditions with variety of defects and defect sizes.

When a new wood specimen is tested, the data set is split into training data which constitutes 80% of the data set and testing data, which constitutes 20% of data set. The training data is further split into X_train and Y_train where X_train has N number of rows and 200 features and Y_train contains N number of rows and one feature namely "Severity" which is the output feature. The defect severity determination module 221 performs "One Hot Encoding" method to map the output feature so as to represent the categorical data (Severity) in binary vectors. The ML model will have 200 input nodes corresponding to 200 input features, X number of hidden layers, and 4 output nodes corresponding to 4 different severities. The ML model uses the efficient "Adam gradient descent" or a similar optimization algorithm with a logarithmic loss function called "categorical crossentropy". The defect severity determination module 221 evaluates the ML model by K-fold cross validation method. The defect severity determination module 221 shuffles the testing data set and creates 10 folds to perform the evaluation. The ML model after getting trained is saved. During testing, the defect severity determination module 221 loads the saved/trained ML model and feeds the new data sample on which it is predicted as to be insignificantly defective, mildly defective, defective, or severely defective.

The wood health record generation module 223: At least one of the condition of the one or more cross-sections of the wood specimen 101, the position of the defect in the one or more cross-sections of the wood specimen 101, the severity of the defect in the one or more cross-sections of the wood specimen 101, and a visual representation of the position of the defect in the one or more cross-sections of the wood specimen 101 are used by the wood health record generation module 223 to generate a health record for the wood specimen 101. This essentially helps for further analysis any time in future and could lead to standardized testing procedures. The wood health record generation module 223 generates a health record at the end of each testing cycle. The health record is cumulatively updated through different test cycles of the wooden specimen 101 under test. In one embodiment, the wood health record generation module 223 stores health record of the wood specimen 101 in the database 103 after every testing. The wood health record generation module 223 can retrieve the health records for the wood specimens anytime.

In one embodiment, the wood health assessment system 107 comprises a defect type determination module (not shown in the FIG. 2a). The defect type determination module determines a type of the defect in the cross-section of the wood specimen 101 using a trained ML model and the relative features of the wood specimen 101 when the condition of the cross-section of the wood specimen 101 is identified to be the defective condition. The training and testing of the ML model are similar to the training and testing of the ML model described for the defect severity determination module 221. The type of the defect in the cross-section of the wood specimen 101 is one of a rot (occurs due to fungi attack), a hole (occurs due to decay) and a knot (occurs due to microorganisms).

Figure 3:
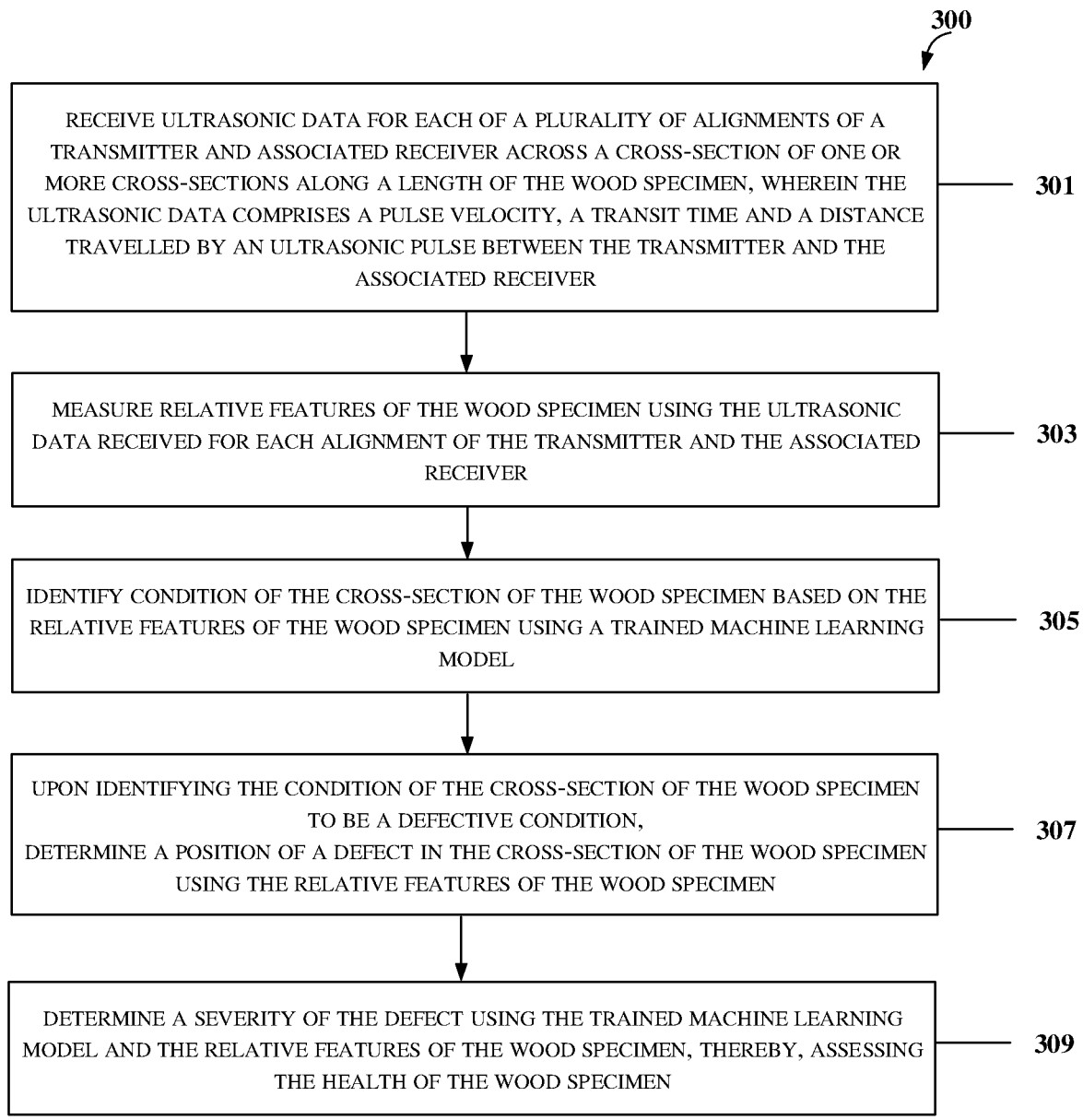
FIG. 3 illustrates a flowchart showing a method of assessing health of a wood specimen in accordance with some embodiments of present disclosure.

FIG. 3 illustrates a flowchart showing a method of assessing health of a wood specimen in accordance with some embodiments of present disclosure.

As illustrated in FIG. 3, the method 300 includes one or more blocks for assessing health of a wood specimen. The method 300 may be described in the general context of computer executable instructions. Generally, computer executable instructions can include routines, programs, objects, components, data structures, procedures, modules, and functions, which perform particular functions or implement particular abstract data types.

The order in which the method 300 is described is not intended to be construed as a limitation, and any number of the described method blocks can be combined in any order to implement the method. Additionally, individual blocks may be deleted from the methods without departing from the scope of the subject matter described herein. Furthermore, the method can be implemented in any suitable hardware, software, firmware, or combination thereof.

At block 301, the ultrasonic data capture and recording module 213 of the wood health assessment system 107 may receive ultrasonic data for each of a plurality of alignments of a transmitter and associated receiver across a cross-section of one or more cross-sections along a length of the wood specimen 101. The ultrasonic data may comprise a pulse velocity, a transit time and a distance travelled by an ultrasonic pulse between the transmitter and the associated receiver.

At block 303, the feature extraction module 215 of the wood health assessment system 107 may measure relative features of the wood specimen 101 using the ultrasonic data received for each alignment of the transmitter and the associated receiver. The relative features may comprise a mean of pulse velocities, a standard deviation of pulse velocities, a lower limit of pulse velocities, an upper limit of pulse velocities, a normalized lower limit of pulse velocities and a normalized upper limit of pulse velocities.

At block 305, the defect detection module 217 of the wood health assessment system 107 may identify a condition of the cross-section of the wood specimen 101 based on the relative features of the wood specimen 101 using a trained machine learning model. The condition of the cross-section of the wood specimen 101 may be one of a defective condition or a non-defective condition.

At block 307, the defect position determination module 219 of the wood health assessment system 107, upon identifying the condition of the cross-section of the wood specimen 101 to be a defective condition, may determine a position of a defect in the cross-section of the wood specimen 101 using the relative features of the wood specimen 101.

At block 309, the defect severity determination module 221 of the wood health assessment system 107 may determine a severity of the defect using the trained machine learning model and the relative features of the wood specimen 101, thereby, assessing the health of the wood specimen 101. The severity of the defect in the cross-section of the wood specimen 101 may be one of insignificantly defective, mildly defective, defective, and severely defective.

Some of the advantages of the present disclosure are listed below.

The present disclosure uses an ultrasonic device for health assessment of a wood specimen, which is a non-destructive testing method.

The present disclosure performs analysis and presents results based on relative measurements/relative features such mean, standard deviation, lower limit, upper limit, normalized lower limit, normalized upper limit and the like and not on absolute values, making the results independent of wood species and avoiding re-training of machine learning model for any new wood species. Consequently, this method leads to more standardised testing and evaluation of any wood specimen.

The method is easy to use for any utility pole inspector/personnel.

Figure 4:
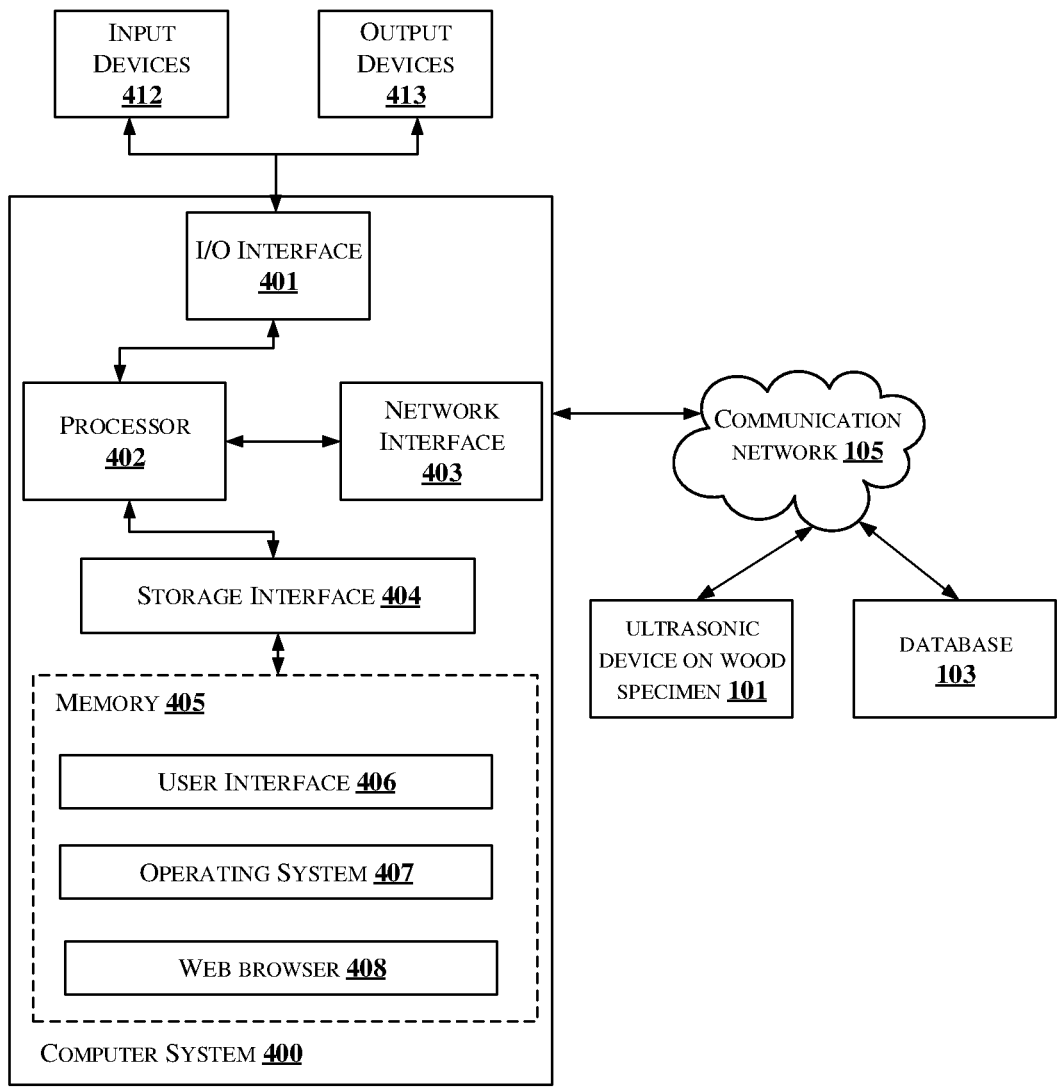
FIG. 4 illustrates a block diagram of an exemplary computer system for implementing embodiments consistent with the present disclosure.

FIG. 4 illustrates a block diagram of an exemplary computer system 400 for implementing embodiments consistent with the present disclosure. In an embodiment, the computer system 400 may be used to implement the wood health assessment system 107. The computer system 400 may include a central processing unit ("CPU" or "processor") 402. The processor 402 may include at least one data processor for assessing health of a wood specimen. The processor 402 may include specialized processing units such as, integrated system (bus) controllers, memory management control units, floating point units, graphics processing units, digital signal processing units, etc.

The processor 402 may be disposed in communication with one or more input/output (I/O) devices (not shown in FIG. 4) via I/O interface 401. The I/O interface 401 employ communication protocols/methods such as, without limitation, audio, analog, digital, monoaural, Radio Corporation of America (RCA) connector, stereo, IEEE®-1394 high speed serial bus, serial bus, Universal Serial Bus (USB), infrared, Personal System/2 (PS/2) port, Bayonet Neill-Concelman (BNC) connector, coaxial, component, composite, Digital Visual Interface (DVI), High-Definition Multimedia Interface (HDMI®), Radio Frequency (RF) antennas, S-Video, Video Graphics Array (VGA), IEEE® 802.11b/g/n/x, Bluetooth, cellular e.g., Code-Division Multiple Access (CDMA), High-Speed Packet Access (HSPA+), Global System for Mobile communications (GSM®), Long-Term Evolution (LTE®), Worldwide interoperability for Microwave access (WiMax®), or the like.

Using the I/O interface 401, the computer system 400 may communicate with one or more I/O devices such as input devices 412 and output devices 413. For example, the input devices 412 may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output devices 413 may be a printer, fax machine, video display (e.g., Cathode Ray Tube (CRT), Liquid Crystal Display (LCD), Light-Emitting Diode (LED), plasma, Plasma Display Panel (PDP), Organic Light-Emitting Diode display (OLED) or the like), audio speaker, etc.

In some embodiments, the computer system 400 consists of the wood health assessment system 107. The processor 402 may be disposed in communication with the communication network 105 via a network interface 403. The network interface 403 may communicate with the communication network 105. The network interface 403 may employ connection protocols including, without limitation, direct connect, Ethernet (e.g., twisted pair 10/100/1000 Base T), Transmission Control Protocol/Internet Protocol (TCP/IP), token ring, IEEE® 802.11a/b/g/n/x, etc. The communication network 105 may include, without limitation, a direct interconnection, Local Area Network (LAN), Wide Area Network (WAN), wireless network (e.g., using Wireless Application Protocol), the Internet, etc. Using the network interface 403 and the communication network 105, the computer system 400 may communicate with the ultrasonic device positioned/aligned on the wood specimen 101 and the database 103. The network interface 403 may employ connection protocols include, but not limited to, direct connect, Ethernet (e.g., twisted pair 10/100/1000 Base T), Transmission Control Protocol/Internet Protocol (TCP/IP), token ring, IEEE® 802.11a/b/g/n/x, etc.

The communication network 105 includes, but is not limited to, a direct interconnection, a Peer to Peer (P2P) network, Local Area Network (LAN), Wide Area Network (WAN), wireless network (e.g., using Wireless Application Protocol), the Internet, Wi-Fi and such.

In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as, Serial Advanced Technology Attachment (SATA), Integrated Drive Electronics (IDE), IEEE®-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user interface 406, an operating system 407, etc. In some embodiments, computer system 400 may store user/application data, such as, the data, variables, records, etc., as described in this disclosure. Such databases may be implemented as fault-tolerant, relational, scalable, secure databases such as Oracle or Sybase.

The operating system 407 may facilitate resource management and operation of the computer system 400. Examples of operating systems include, without limitation, APPLE® MACINTOSH® OS X®, UNIX®, UNIX-like system distributions (E.G., BERKELEY SOFTWARE DISTRIBUTION® (BSD), FREEBSD®, NETBSD®, OPENBSD, etc.), LINUX® DISTRIBUTIONS (E.G., RED HAT®, UBUNTU®, KUBUNTU®, etc.), IBM®OS/2®, MICROSOFT® WINDOWS® (XP®, VISTA®/7/8, 10 etc.), APPLE® IOS®, GOOGLE™ ANDROID™, BLACK-BERRY® OS, or the like.

In some embodiments, the computer system 400 may implement web browser 408 stored program components. Web browser 408 may be a hypertext viewing application, such as MICROSOFT® INTERNET EXPLORER®, GOOGLE™ CHROME™, MOZILLA® FIREFOX®, APPLE® SAFARI®, etc. Secure web browsing may be provided using Secure Hypertext Transport Protocol (HTTPS), Secure Sockets Layer (SSL), Transport Layer Security (TLS), etc. Web browsers 408 may utilize facilities such as AJAX, DHTML, ADOBE® FLASH®, JAVASCRIPT®, JAVA®, Application Programming Interfaces (APIs), etc. The computer system 400 may implement a mail server (not shown in FIG. 4) stored program component. The mail server may be an Internet mail server such as Microsoft Exchange, or the like. The mail server may utilize facilities such as ASP, ACTIVEX®, ANSI® C++/C #, MICROSOFT®, .NET, CGI SCRIPTS, JAVA®, JAVASCRIPT®, PERL®, PHP, PYTHON®, WEBOBJECTS®, etc. The mail server may utilize communication protocols such as Internet Message Access Protocol (IMAP), Messaging Application Programming Interface (MAPI), MICROSOFT® exchange, Post Office Protocol (POP), Simple Mail Transfer Protocol (SMTP), or the like. The computer system 400 may implement a mail client (not shown in FIG. 4) stored program component. The mail client may be a mail viewing application, such as APPLE® MAIL, MICROSOFT® ENTOURAGE®, MICROSOFT® OUTLOOK®, MOZILLA® THUNDERBIRD®, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media include all computer-readable media except for a transitory. The code implementing the described operations may further be implemented in hardware logic (e.g., an integrated circuit chip, Programmable Gate Array (PGA), Application Specific Integrated Circuit (ASIC), etc.).

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary, a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 3 show certain events occurring in a certain order. In alternative embodiments, certain operations may be performed in a different order, modified or removed. Moreover, steps may be added to the above-described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

REFERRAL NUMERALS:

| Reference number | Description |
| --- | --- |
| 100 | Environment |
| 101 | Wood specimen |
| 103 | Database |
| 105 | Communication network |
| 107 | Wood health assessment system |
| 111 | I/O interface |
| 113 | Memory |
| 115 | Processor |
| 200 | Data |
| 201 | Ultrasonic data |
| 203 | Other data |
| 211 | Modules |
| 213 | Ultrasonic data capture and recording module |
| 215 | Feature extraction module |
| 217 | Defect detection module |
| 219 | Defect position determination module |
| 221 | Defect severity determination module |
| 223 | Wood health record generation module |
| 225 | Other modules |
| 400 | Computer system |
| 401 | I/O interface |
| 402 | Processor |
| 403 | Network interface |
| 404 | Storage interface |
| 405 | Memory |
| 406 | User interface |
| 407 | Operating system |
| 408 | Web browser |
| 412 | Input devices |
| 413 | Output devices |

What is claimed is:

1. A method of assessing health of a wood specimen of a utility pole, the method comprising:

aligning, by an ultrasonic data capture and recording module of a wood health assessment system, an ultrasonic device, comprising a transmitter and an associated receiver, to be positioned along a plurality of alignments, wherein the plurality of alignments being defined between a plurality of points;

receiving, by the ultrasonic data capture and recording module of the wood health assessment system, ultrasonic data from the ultrasonic device for each of the plurality of alignments of the transmitter and the associated receiver across a cross-section of one or more cross-sections along a length of the wood specimen of the utility pole, wherein for each of the plurality of points, the ultrasonic data associated with each adjacent point from the plurality of points is excluded, and wherein the ultrasonic data comprises a pulse velocity, a transit time, and a distance travelled by an ultrasonic pulse between the transmitter and the associated receiver;

measuring, by a feature extraction module of the wood health assessment system, relative features of the wood specimen of the utility pole using the ultrasonic data received for each alignment of the transmitter and the associated receiver, wherein the relative features comprise a mean of pulse velocities, a standard deviation of pulse velocities, a lower limit of pulse velocities, an upper limit of pulse velocities, a normalized lower limit of pulse velocities, and a normalized upper limit of pulse velocities;

training, by the wood health assessment system, a machine learning model using the relative features and at least one of a Support Vector Machine (SVM) model, a Random Forest model, and a Logical Regression model to generate a trained machine learning model;

identifying, by a defect detection module of the wood health assessment system, a condition of the cross-section of the wood specimen of the utility pole based on the relative features of the wood specimen of the utility pole using the trained machine learning model;

upon identifying the condition of the cross-section of the wood specimen of the utility pole to be a defective condition, determining, by a defect position determination module of the wood health assessment system, a position of a defect in the cross-section of the wood specimen of the utility pole using the relative features of the wood specimen of the utility pole; and determining, by a defect severity determination module of the wood health assessment system, a severity of the defect using the trained machine learning model and the relative features of the wood specimen of the utility pole, thereby, assessing the health of the wood specimen of the utility pole; and generating, by a wood health record generation module of the wood health assessment system, a health record for the wood specimen of the utility pole, wherein the health record comprises at least one of the condition of the cross-section of the wood specimen of the utility pole, the position of the defect in the cross-section of the wood specimen of the utility pole, the severity of the defect, and a visual representation of the position of the defect in the cross-section of the wood specimen of the utility pole.

2. The method as claimed in claim 1, wherein the condition of the cross-section of the wood specimen of the utility pole is one of the defective condition or a non-defective condition.

3. The method as claimed in claim 1, wherein the severity of the defect in the cross-section of the wood specimen of the utility pole is one of insignificantly defective, mildly defective, defective, and severely defective.

4. A wood health assessment system for assessing health of a wood specimen of a utility pole, the wood health assessment system comprising:

a processor; and a memory communicatively coupled to the processor, wherein the memory stores processor-executable instructions, which on execution, cause the processor to:

align, by an ultrasonic data capture and recording module, an ultrasonic device, comprising a transmitter and an associated receiver, to be positioned along a plurality of alignments, wherein the plurality of alignments being defined between a plurality of points;

receive, by an ultrasonic data capture and recording module, ultrasonic data from the ultrasonic device for each of the plurality of alignments of the transmitter and the associated receiver across a cross-section of one or more cross-sections along a length of the wood specimen of the utility pole, wherein for each of the plurality of points, the ultrasonic data associated with each adjacent point from the plurality of points is excluded, and wherein the ultrasonic data comprises a pulse velocity, a transit time, and a distance travelled by an ultrasonic pulse between the transmitter and the associated receiver;

measure, by a feature extraction module, relative features of the wood specimen of the utility pole using the ultrasonic data received for each alignment of the transmitter and the associated receiver, wherein the relative features comprise a mean of pulse velocities, a standard deviation of pulse velocities, a lower limit of pulse velocities, an upper limit of pulse velocities, a normalized lower limit of pulse velocities, and a normalized upper limit of pulse velocities;

train a machine learning model using the relative features and at least one of a Support Vector Machine (SVM) model, a Random Forest model, and a Logical Regression model to generate a trained machine learning model;

identify, by a defect detection module, a condition of the cross-section of the wood specimen of the utility pole based on the relative features of the wood specimen of the utility pole using the trained machine learning model;

upon identifying the condition of the cross-section of the wood specimen of the utility pole to be a defective condition,
  determine, by a defect position determination module, a position of a defect in the cross-section of the wood specimen of the utility pole using the relative features of the wood specimen of the utility pole; and
  determine, by a defect severity determination module, a severity of the defect using the trained machine learning model and the relative features of the wood specimen of the utility pole, thereby, assessing the health of the wood specimen of the utility pole; and generate, by a wood health record generation module of the wood health assessment system, a health record for the wood specimen of the utility pole, wherein the health record comprises at least one of the condition of the cross-section of the wood specimen of the utility pole, the position of the defect in the cross-section of the wood specimen of the utility pole, the severity of the defect, and a visual representation of the position of the defect in the cross-section of the wood specimen of the utility pole.

5. The wood health assessment system as claimed in claim 4, wherein the condition of the cross-section of the wood specimen of the utility pole is one of the defective condition or a non-defective condition.

6. The wood health assessment system as claimed in claim 4, wherein the severity of the defect in the cross-section of the wood specimen of the utility pole is one of insignificantly defective, mildly defective, defective, and severely defective.

7. A non-transitory computer readable medium including instructions stored thereon that when processed by at least one processor cause a wood health assessment system to perform operations comprising:

aligning an ultrasonic device, comprising a transmitter and an associated receiver, to be positioned along a plurality of alignments, wherein the plurality of alignments being defined between a plurality of points;

receiving ultrasonic data from the ultrasonic device for each of the plurality of alignments of the transmitter and the associated receiver across a cross-section of one or more cross-sections along a length of a wood specimen of a utility pole, wherein for each of the plurality of points, the ultrasonic data associated with each adjacent point from the plurality of points is excluded, and wherein the ultrasonic data comprises a pulse velocity, a transit time, and a distance travelled by an ultrasonic pulse between the transmitter and the associated receiver;

measuring relative features of the wood specimen of the utility pole using the ultrasonic data received for each alignment of the transmitter and the associated receiver, wherein the relative features comprise a mean of pulse velocities, a standard deviation of pulse velocities, a lower limit of pulse velocities, an upper limit of pulse velocities, a normalized lower limit of pulse velocities, and a normalized upper limit of pulse velocities;

training, by the wood health assessment system, a machine learning model using the relative features and at least one of a Support Vector Machine (SVM) model, a Random Forest model, and a Logical Regression model to generate a trained machine learning model;

identifying a condition of the cross-section of the wood specimen of the utility pole based on the relative features of the wood specimen of the utility pole using the trained machine learning model;

upon identifying the condition of the cross-section of the wood specimen of the utility pole to be a defective condition,
  determining a position of a defect in the cross-section of the wood specimen of the utility pole using the relative features of the wood specimen of the utility pole; and
  determining a severity of the defect using the trained machine learning model and the relative features of the wood specimen of the utility pole, thereby, assessing the health of the wood specimen of the utility pole; and generating, by a wood health record generation module, a health record for the wood specimen of the utility pole, wherein the health record comprises at least one of the condition of the cross-section of the wood specimen of the utility pole, the position of the defect in the cross-section of the wood specimen of the utility pole, the severity of the defect, and a visual representation of the position of the defect in the cross-section of the wood specimen of the utility pole.

8. The medium as claimed in claim 7, wherein the condition of the cross-section of the wood specimen of the utility pole is one of the defective condition or a non-defective condition.

9. The medium as claimed in claim 7, wherein the severity of the defect in the cross-section of the wood specimen of the utility pole is one of insignificantly defective, mildly defective, defective, and severely defective.

* * * * *